United States Patent [19]

Miyashita

[11] Patent Number: 5,467,188
[45] Date of Patent: Nov. 14, 1995

[54] PARTICLE DETECTION SYSTEM

[75] Inventor: Haruzo Miyashita, Tokyo, Japan

[73] Assignee: Anelva Corporation, Tokyo, Japan

[21] Appl. No.: 293,065

[22] Filed: Aug. 19, 1994

[30] Foreign Application Priority Data

Aug. 20, 1993  [JP]  Japan .................................. 5-228332

[51] Int. Cl.$^6$ .................................................. G01N 15/02
[52] U.S. Cl. ........................................ 356/336; 356/339
[58] Field of Search ................................ 356/335–343, 356/244, 246; 250/574, 576, 492.2, 492.3, 397

[56] References Cited

U.S. PATENT DOCUMENTS

| | | | |
|---|---|---|---|
| 4,387,993 | 6/1983 | Adrian | 356/336 |
| 4,420,256 | 12/1983 | Fladda et al. | 356/336 |
| 4,571,079 | 2/1986 | Knollenberg | 356/336 |
| 4,573,796 | 3/1986 | Martin et al. | 356/318 |
| 4,680,977 | 7/1987 | Conero et al. | 356/338 |
| 4,728,190 | 3/1988 | Knollenberg | 356/336 |
| 4,739,177 | 4/1988 | Borden | 250/574 |
| 4,781,459 | 11/1988 | Suzuki | 356/335 |
| 4,783,599 | 11/1988 | Borden | 250/574 |
| 4,792,199 | 12/1988 | Borden | 356/37 |
| 4,798,465 | 1/1989 | Knollenberg | 356/336 |
| 4,804,853 | 2/1989 | Borden et al. | 250/574 |
| 4,825,094 | 4/1989 | Borden et al. | 250/573 |
| 4,893,928 | 1/1990 | Knollenberg | 356/336 |
| 4,896,048 | 1/1990 | Borden | 250/574 |
| 5,055,698 | 10/1991 | Borden | 250/574 |
| 5,084,614 | 1/1992 | Berkner | 250/227.11 |
| 5,085,500 | 2/1992 | Blesener | 356/338 |
| 5,121,988 | 6/1992 | Blesener et al. | 356/442 |
| 5,132,548 | 7/1992 | Borden et al. | 250/574 |
| 5,157,678 | 10/1992 | Borden | 372/34 |
| 5,235,625 | 8/1993 | Stoltz et al. | 377/10 |
| 5,271,264 | 12/1993 | Chanayem | 73/28.01 |
| 5,282,151 | 1/1994 | Knollengerg | 364/555 |

OTHER PUBLICATIONS

U.S. Pat. No. 5,083,865 (Gazette, Jan. 28, 1992, p. 2103).
Busselman et al, "In Situ Particle Monitoring in a Single Wafer Poly Silicon and Silicon Nitride Etch System", 1993 IEEE/SEMI Int'l Semiconductor Manufacturing Science Symposium, pp. 20–26.
Peters, "20 Good Reasons to Use In Situ Particle Monitors", Semiconductor International, Nov. 1992, pp. 52–57.

*Primary Examiner*—Hoa Q. Pham
*Attorney, Agent, or Firm*—Sughrue, Mion, Zinn, Macpeak & Seas

[57] ABSTRACT

A particle detecting system for detecting the number and size of particles generated in a process chamber of a semiconductor manufacturing system. The particle detecting system includes a small detection chamber and a particle detector. The small detection chamber not only has an internal space thereof provided outside a wall portion forming the process vacuum chamber so as to communicate with the process vacuum chamber, but also laser beam transmitting windows and scattered light extracting windows. The particle detector is arranged in an atmospheric environment outside the detection chamber and including a laser diode for emitting a laser beam into the detection chamber through the laser beam transmitting windows and photosensors for detecting scattered light generated within the detection chamber through the scattered light extracting windows. The detection chamber has such a structure as to be detachably attached to the process chamber. The particle detector is formed as a module, and can be attached to the detection chamber from outside the detection chamber. The particle detector has such a structure as to be detachably attached to the detection chamber.

9 Claims, 4 Drawing Sheets

PARTICLE DETECTION SYSTEM

BACKGROUND OF THE INVENTION

1. Field of the Invention

The present invention relates to particle detection systems and, more particularly, to a particle detection system for detecting particles such as dust particles generated within semiconductor manufacturing systems.

2. Description of Conventional Art

In current semiconductor manufacturing processes, yields determine the price and reliability of products. Dust particles generated within a semiconductor manufacturing system have a considerable affect on yields, therefore the amount of dust generated within the semiconductor manufacturing system must be minimized in order to improve the yields. In other words, when semiconductor devices are produced in an environment containing a large amount of dust particles, the probability that the particles of dust adhere to wafers increases. As a result, product defects such as defective wiring patterns on the wafers increase, thereby decreasing yields. In the majority of currently used semiconductor manufacturing systems, dust particles are generated within the process chamber in the course of manufacturing the products, and the dust particles gradually accumulate in the process chamber. When the amount of dust particles exceeds a predetermined threshold value, product yield decreases below a predetermined value. As a result, profit is low even if the products are sold. Therefore, in the manufacture of semiconductor products it is necessary to always keep the amount of dust particles generated within the semiconductor manufacturing system under control and maintain the semiconductor manufacturing system when the number of particles exceeds the above-mentioned predetermined number (threshold) to remove the dust particles accumulated in the process chamber.

Among generally employed conventional methods of detecting particles such as dust is the light scattering method, which involves the steps of detecting, by means of a light-detection element, scattered light generated when a laser beam is radiated onto dust and measuring the number, size, etc. of the particles.

The light scattering method is also employed to measure dust generation within the semiconductor manufacturing system. A small-sized particle flux monitor disclosed in U.S. Pat. No. 4,804,853 is a prior art example employing the light scattering method for detecting dust in a semiconductor manufacturing system. The small-sized particle flux monitor disclosed in this patent is designed to measure the number and size of dust particles by focusing a laser beam emitted from a laser diode onto a dust detecting zone with a converging lens, scattering the laser beam when dust passes across the beam, and collecting the scattered light by means of photodiodes.

U.S. Pat. No. 4,739,177 proposes a particle detection system in which the probability of particle detection is improved by forming a laser beam net with a laser beam reflected between two mirrors. Further, U.S. Pat. No. 5,132,548 proposes a particle detecting system in which the probability of particle detection is improved by forming a sheet-like laser beam by means of a combination of prisms.

Since, generally, all the detecting system parts must be mounted and used inside the process vacuum chamber, a particle detecting system for detecting particles in a vacuum raises the following problems.

First, in the case of measuring particles in an etching gas environment such as a plasma etching system, the laser diode, lens, photodiodes, and the like mounted inside the detecting system deteriorate and shorten the lifetime of the detecting system to a significant degree. Further, these optical parts and the like are not only extremely expensive but also of high precision, so that a considerable amount of expense and labor are entailed in repairing them.

Still further, plasma CVD and sputtering systems are designed to deposit films by heating the wafer and the like, which subjects the process chamber to temperatures as high as several hundred degrees celsius. Parts of the detection system break at such high temperatures.

The above-mentioned small-sized particle flux monitor disclosed in U.S. Pat. No. 4,804,853 is mainly designed to detect floating particles in a gas or liquid with high responsivity. Therefore, such a monitor is not well suited to detect particles in a vacuum. Further, the detection systems according to U.S. Pat. Nos. 4,739,177 and 5,132,548 are of such a type that the sensor itself is installed in the process chamber. If these detection systems are mounted in the vacuum of the process chamber as they are, the detection systems themselves liberate gas, possibly adversely affecting the semiconductor products.

Further, if the above-mentioned detecting systems are used at high temperatures, the laser diode will fail, making it difficult to measure the dust within the process chamber of a plasma CVD or sputtering system. Still further, if the sensor is disposed within the process chamber in which a reactive gas is used such as in the process chamber of an etching system, the optical parts, including the lens in the sensor, may be eroded.

Still further, in order to maintain and repair the sensor, the process chamber must be exposed to the outer atmosphere, which entails a great deal of time and labor.

Dust particles are generated most in the process vacuum chamber such as the film deposition chamber or the etching chamber in the semiconductor manufacturing system. Therefore, the highest priority must be given to control of the generation of dust particles in the process chamber. While conventional dust particle detection systems can measure dust particles in the process chamber as described above, these systems cannot be used in reactive gas environments such as those used in etching systems or high temperature environments such as those used in plasma CVD systems.

SUMMARY OF THE INVENTION

An object of the present invention is to provide a particle detection system capable of detecting the number and size of particles generated in a process chamber of a semiconductor manufacturing system or the like, and measuring the particles stably without being affected by the kinds of gases used and process temperatures applied in the process chamber. Another object of the present invention is to provide a particle detection system which ensures easy maintenance and installation in the semiconductor manufacturing system.

To achieve the above objects, the present invention is applied to a particle detection system for detecting the number and size of particles generated at a process chamber in which a process is performed. Such a particle detection system includes: a detection chamber not only having an internal space thereof provided outside a wall portion forming the process chamber so as to communicate with the process chamber, but also having a laser beam transmitting window and a scattered light extracting window; and a particle detector arranged in the outer atmosphere outside the detection chamber and including a light-emission means for irradiating a laser beam into the detection chamber through the laser beam transmitting window and a light-detection means for detecting scattered light generated within the detection chamber through the scattered light extracting window.

In the above construction, the detection chamber preferably has a structure which enables it to be attached to and detached from the process chamber.

In the above construction, the particle detector is preferably formed as a module, attached to the detection chamber from outside, and has a structure which enables it to be attached to and detached from the detection chamber.

In the above construction, the particle detector is preferably attached to the detection chamber by fitting the detection chamber into an opening formed in the case of the particle detector.

In the above construction, the light-detection means is preferably arranged in such a position as to detect scattered light generated at an angle close to 90° with respect to the laser beam path.

In the above construction, the light-detection means is preferably arranged in such a position as to detect scattered light generated at an angle within a range of from 10 to 70 degrees with respect to the laser beam path.

In the above construction, the laser beam transmitting window preferably includes a laser beam entrance window and a laser beam exit window, with the laser beam exit window also being used as the scattered light extraction window.

The present invention comprises a particle detection system that detects particles suspended within the process chamber of a semiconductor manufacturing system or the like in which the wafer processing is performed, on the atmospheric side outside the process chamber. Such a particle detection system has a small detection chamber that is attached to the process chamber and in which measurements are made. The detection chamber has a laser beam entrance window and a laser beam exit window (these windows are laser beam transmitting windows), and scattered light extraction windows that guide a laser beam scattered by particles out of the detection chamber. The particles within the process chamber are detected in the following way. The scattered light generated when the particles transported from the process chamber to the detection chamber pass across the laser beam is extracted from the detection chamber through the scattered light extraction windows and detected by photosensors. The locations of the photosensors are selected from locations where the scattered light is detected most efficiently.

The particle detection system of the present invention is also characterized in that the sensor section, which includes optical components and the like and which has a complicated structure, is arranged on the outer atmosphere side. Therefore, even if failure occurs in this section, this section can be subjected to maintenance without exposing the process chamber to the air.

DETAILED DESCRIPTION OF THE PREFERRED EMBODIMENTS

Figure 1:
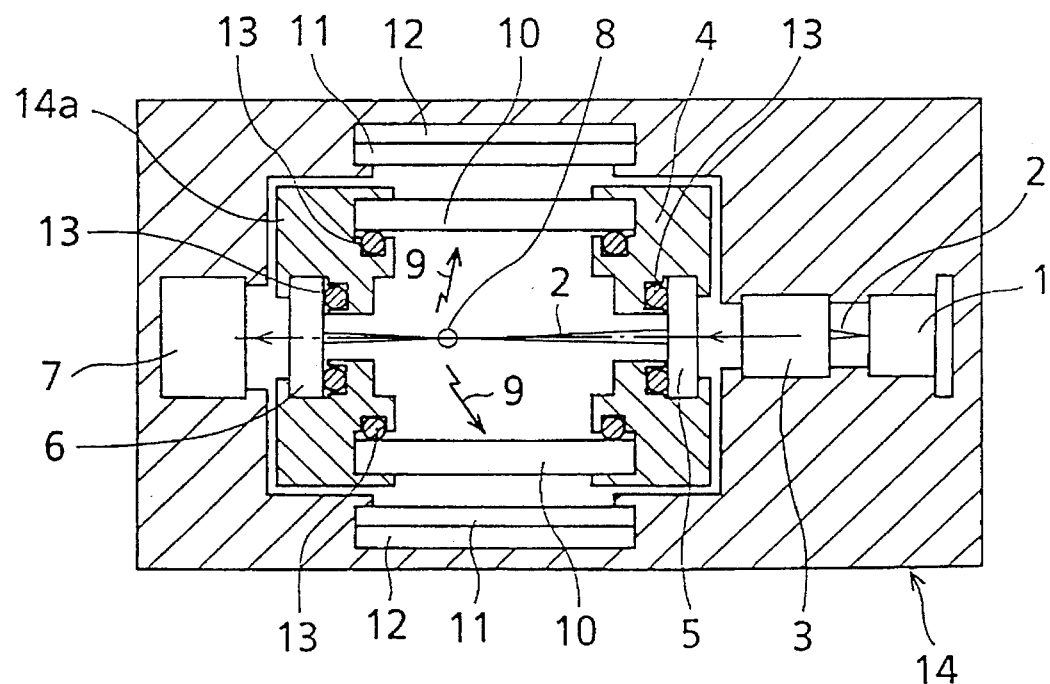
FIG. 1 is a sectional view showing the main structure of a particle detection system according to an embodiment of the present invention.

Preferred embodiments of the present invention will now be described with reference to the accompanying drawings. FIG. 1 is a sectional view showing the main structure of a particle detection system of the invention; and FIG. 2 is a perspective view showing the appearance of the particle detection system for explaining how the particle detection system is attached.

The particle detection system of the present invention includes a small detection chamber (hereinafter referred to as "detection chamber") and a particle detector unit attached to this detection chamber. The detection chamber is mounted outside an enclosure forming a process chamber in which a semiconductor manufacturing system process (wafer process) is performed.

Figure 2:
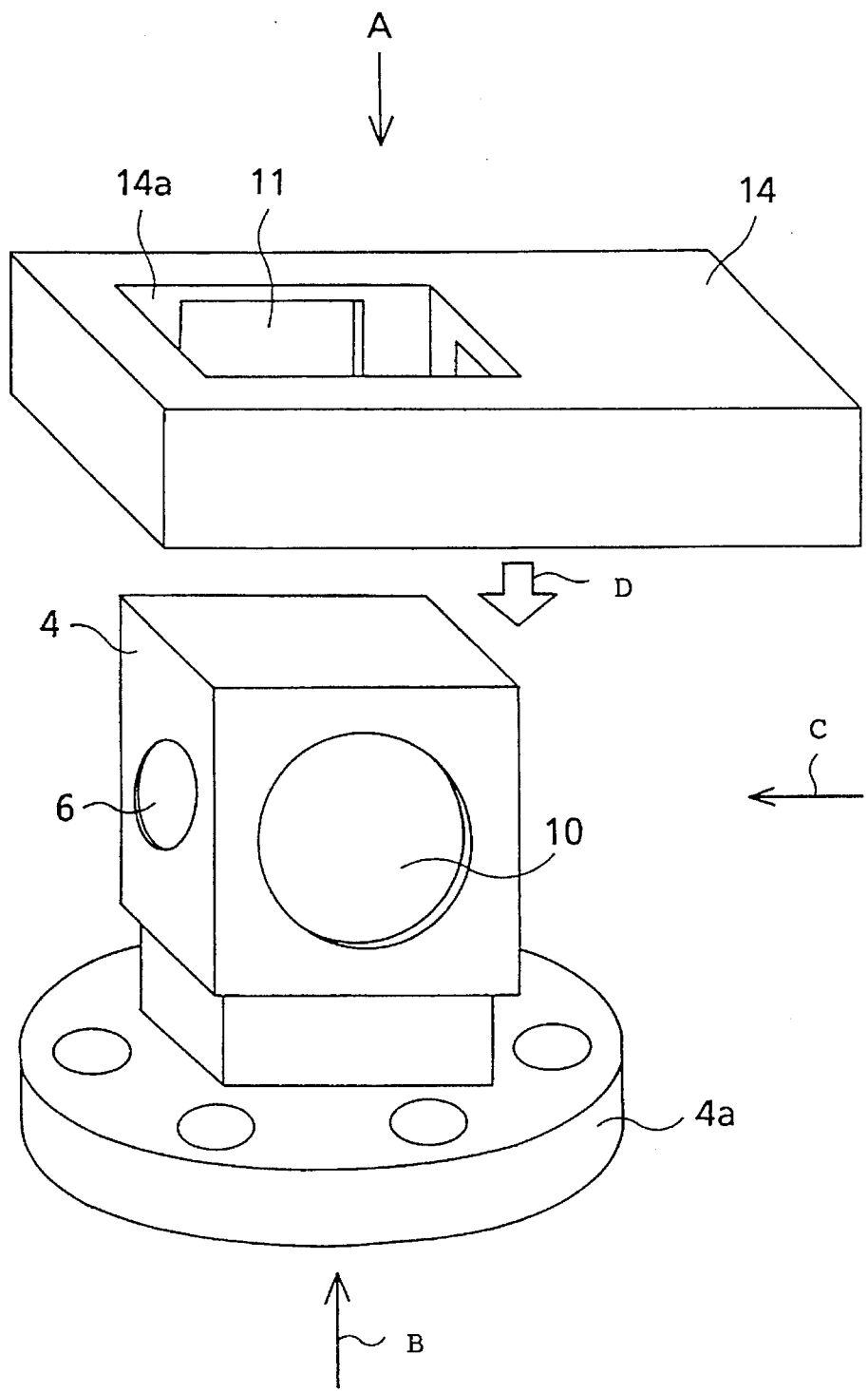
FIG. 2 is a perspective view showing the appearance of the particle detection system, for explaining how the particle detection system is attached.

In FIG. 2, reference numeral 4 denotes the detection chamber. The lower portion of the detection chamber 4 is of a vacuum flange structure. The detection chamber 4 is attached to the outside of the wall portion of the process chamber of a semiconductor manufacturing system (not shown) by a flange 4a thereof. The internal space of the detection chamber 4 communicates with the process chamber of the semiconductor manufacturing system through an opening (not shown). It is structurally easy to attach the detection chamber 4 to the wall portion of the process chamber case of the semiconductor manufacturing system. The detection chamber 4 can be attached to and detached from the process chamber. This attach/detach structure can employ arbitrary structure. In FIG. 2 the space below the detection chamber 4 is the process chamber. As shown in FIG. 2, the detection chamber 4 is (for example) cubic and has a laser beam entrance window 5 (shown in FIG. 1) and a laser beam exit window 6 formed in two opposed sidewalls. Scattered light entrance windows 10 are formed in the two remaining opposed sidewalls. The laser beam entrance window 5 and the laser beam exit window 6 transmit a laser beam.

In FIG. 2 the arrow B indicates the direction in which particles (particles of dust and the like to be subjected to measurement) transported from the process chamber side advance, and the arrow C indicates the direction in which a laser beam is emitted. The internal space of the detection chamber 4 communicates with the process chamber through the opening, and is kept in an evacuated condition (vacuum) the same as the interior of the process chamber. The particles enter into the internal space of the detection chamber 4 via the opening.

The particle detection unit 14 is attached to the thus formed detection chamber 4. The particle detection unit 14 in this embodiment is formed as a module independent of the detection chamber 4, and has a form and structure which is attachable to and detachable from the detection chamber 4. However, the structure of the particle detector unit is not limited to the above, but may be of such a structure as to be combined with the detection chamber 4. An enclosure forming the exterior of the particle detection unit 14 has a substantially square opening 14a at a predetermined position. This opening 14a is a hole that passes through the case of the particle detection unit 14 from the upper surface to the lower surface as shown in FIG. 2. To attach the particle detection unit 14 to the detection chamber 4, the opening 14a is so positioned as to be fitted to the detection chamber 4 as indicated by the arrow D in FIG. 2. In this attached state, the particle detection unit 14 is fixed to the detection chamber 4 by a connecting means (not shown). That is, the particle detection unit 14 is additionally attached to the outside portion (on the atmospheric side) of the detection chamber 4.

Then, referring to FIG. 1, the internal structure of the particle detection unit 14 and the internal structure of the detection chamber 4, as well as how particles are detected, will be described. FIG. 1 shows in section the respective internal structures of the particle detection unit 14 and the detection chamber 4 as viewed in the direction A in FIG. 2. Referring to FIG. 1, which shows the detection chamber 4 fitted into the opening 14a of the particle detection unit 14, the internal structure of the particle detection unit 14 will be described together with the related internal structure of the detection chamber 4.

In the particle detection unit 14, reference numeral 1 denotes a laser diode (light-emission means), for which a semiconductor laser SLD201-3 having an optical output of 50 mW (manufactured by Sony Corporation) may be used, for example. A laser beam 2 emitted from this laser diode 1 is corrected into parallel beams or spot-like beams by a collimator lens 3. A cylindrical lens may be added to the collimator lens 3 to form a sheet-like beam. Detection probability can be improved by use of a sheet-like beam.

The laser beam 2 having passed through the collimator lens 3, is emitted from the laser beam entrance window 5 attached to the detection chamber 4 through the detection chamber 4, exiting at a position opposite the introduction side through the laser beam exit window 6. A light absorber 7 is disposed at this opposite position, into which the laser beam 2, having exited from the laser beam exit window 6, is irradiated. The light absorber 7 is arranged to prevent unnecessary light from leaking out, incurring particle measurement errors. The light absorber 7 terminates the irradiated light.

Let it now be assumed that a particle has entered the detection chamber 4 from the process chamber in the direction of the arrow B shown in FIG. 2. Reference numeral 8 in FIG. 1 denotes the particle, passing across the laser beam 2. If the particle 8 traverses the laser beam 2 which passes through the detection chamber 4, it causes light scattering. A portion of scattered light 9 comes out through the scattered light exit windows 10 disposed on the sides of the detection chamber 4, and passes through optical filters 11 disposed on the particle detection unit 14. The scattered light 9 is detected by two photosensors which form detection means) 12 arranged within the unit. The photosensors 12 are arranged on opposite sides respectively, as shown in FIG. 1. The photosensors 12 in this embodiment are so arranged that the light-detection surfaces thereof are parallel to the direction in which laser beam 2 travels (optical axis). Hence, these photodiodes 12 detect the portion (scattered light 9) of the scattered light generated in a direction at substantially right angles to the direction of the laser beam 2. From the frequency and intensity of light scattered by the particle 8, the number and size of particles entering to the detection chamber 4 from the direction of the process chamber of the semiconductor manufacturing system can be measured. In FIGS. 1 and 2 a processing circuit which processes the detection signals of the photosensors 12 is not shown.

The optical filters 11 arranged in front of the detection surfaces of the respective photosensors 12 prevent light whose wavelength is different from that of the scattered light of the laser beam from being detected by the photosensors 12. In other words, the optical filters 11 prevent interference of various rays of light as stray light in an environment in which the particle detecting system is used to eliminate particle measurement errors.

The detection chamber 4 has, as described above, the laser beam entrance window 5, the laser beam exit window 6, and the scattered light exit windows 10. These windows are coated with films to prevent reflection. It is necessary for the materials of which these windows 5, 6, 10 are made to have high transmittance with respect to the wavelength of the laser beam 2. These windows 5, 6, 10 are vacuum-sealed by O-rings 13 to maintain airtightness.

As described above, the internal space of the detection chamber 4 is a vacuum. The effect of drag force on the behavior of particles decreases with the environmental pressure. Therefore, particles within the process chamber enter the detection chamber 4 at high speed. The particle 8 generates the scattered light 9 by passing across the laser beam 2 emitted from the laser diode 1, and the scattered light 9 is detected by the photosensors 12.

In the case of applying the particle detection system of the invention to a plasma etching system in which a corrosive gas is used in the processing chamber, such important parts as the laser diode 1 and the photosensors 12 are arranged on the outer atmosphere side, incorporated into the particle detector unit 14 as described above. Therefore, it is not likely that these expensive parts will be deteriorated by the corrosive gas, nor is it likely that the laser diode 1 and the like will be extraordinarily heated if the temperature in the process chamber is very high. Even when there is the possibility that the laser diode 1 and the like are heated by the high temperature of the process chamber, water cooling means or air cooling means can be easily provided because the laser diode 1 is located on the outer atmosphere side.

Further, the particle detection system of the invention is excellent in terms of maintenance. When the particle detection system is used over a long period of time, particles may possibly accumulate within the detection chamber. What is needed to be done as maintenance of the particle detecting system of the invention is merely to remove the detection chamber 4 from the process chamber of the semiconductor manufacturing system and clean the four windows. When a corrosive gas is used, it is thought that the light transmittance of these windows will be impaired. In this case, the windows may simply be replaced with recycled windows. The old windows can be recycled by, e.g., polishing and surface treatment while the newly attached windows are being used. As a result, the running cost of the particle detecting system can be reduced. Further, the particle detector unit 14 can be maintained without exposing the process chamber and the detection chamber to the outside air.

Figure 3:
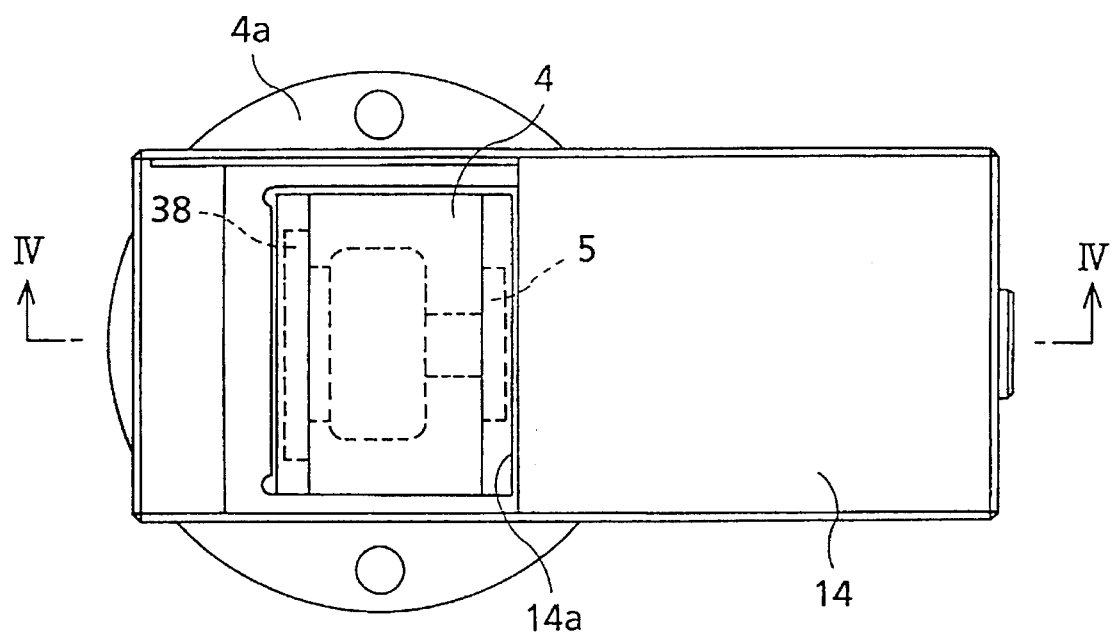
FIG. 3 is a plan view showing a particle detection system according to another embodiment of the present invention.
Figure 4:
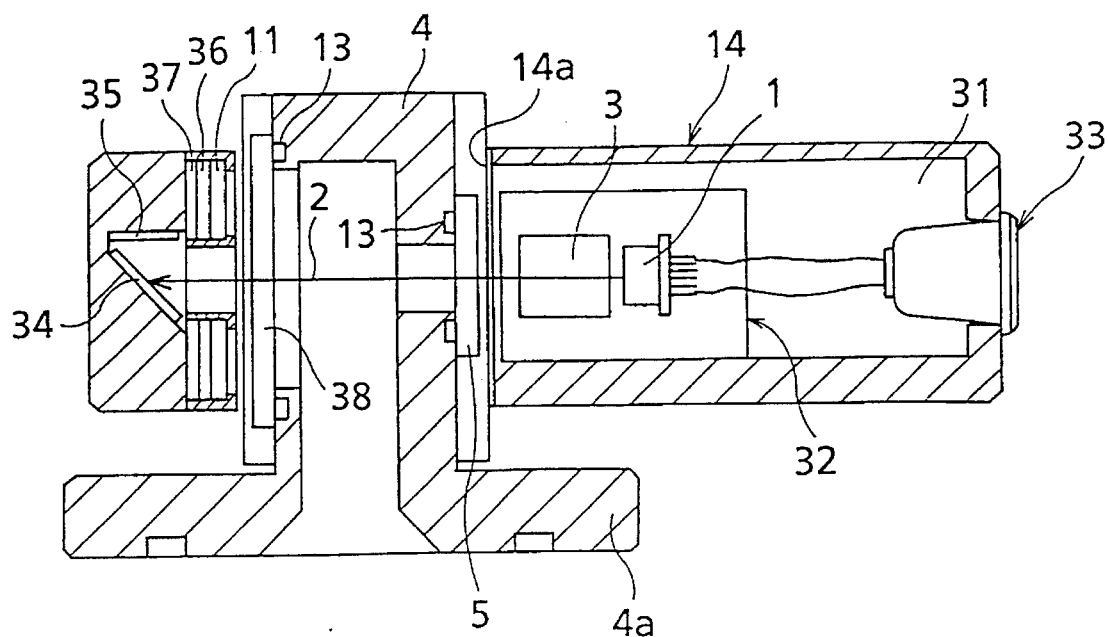
FIG. 4 is a sectional view taken along a line IV—IV of FIG. 3 showing the internal structure of the particle detection system shown in FIG. 3.
Figure 5:
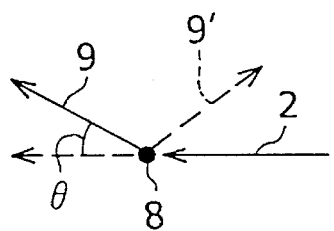
FIG. 5 is a diagram showing a range of angles of scattered light.

Another embodiment of the present invention will be described with reference to FIGS. 3 and 4. FIG. 3 is a plan view of the embodiment and FIG. 4 is a sectional view taken along a line IV—IV of FIG. 3. This embodiment is characterized in that it improves detection sensitivity by changing the position at which the photosensors for detecting scattered light are disposed. In FIGS. 3 and 4 elements substantially the same as those of the above-mentioned embodiment are denoted by the same reference numerals.

A particle detection unit 14 has an opening 14a to be fitted with the detection chamber 4, and in a hollow portion 31 thereof are a laser emission unit 32 and a connector 33. The laser emission unit 32 incorporates a laser diode 1 and a collimator lens 3. The connector 33 and the laser diode 1 are connected by electrical wiring. Power supplied from an external source is applied to the laser diode 1 through the connector 33. Light absorbers are provided at a portion opposite the hollow portion 31 in such a manner that the opening 14a is positioned therebetween. This embodiment has two light absorbers 34 and 35. The first light absorber 34 is disposed at an inclination of, e.g., 45° with respect to the optical axis of the laser beam 2 emitted from the laser emission unit 32, and the second light absorber 35 is located at such a position as to receive the laser beam reflected by the first light absorber 34. The total absorption coefficient for the laser beam is increased by the combined use of the two light absorbers 34 and 35.

A photosensor 36 is arranged at the side of the light absorbers 34, 35; specifically, surrounding the optical axis of the laser beam 2 on the opening 14a side and in front of the light absorber 34. The photosensor 36 is so arranged that the light detection surface thereof is at substantially right angles to the path of the laser beam 2. The light-detection surface of the photosensor 36 faces the internal space of the detection chamber 4 with an optical filter 11 provided in front thereof. On the back of the photosensor 36 is a cushion rubber 37.

In the thus-constructed particle detector unit 14 the structure of the detection chamber 4 which is fitted into the opening 14a is basically the same as that described in the above-mentioned embodiment. What characterizes the detection chamber 4 in this embodiment is that the scattered light exit window is not provided, but the laser beam exit window doubles as the scattered light exit window. In FIG. 4, reference numeral 38 denotes a laser beam exit window serving also as the scattered light exit window. This window 38 has a relatively large area. Reference numeral 5 denotes a laser beam entrance window; and 13, an O-ring.

The above-mentioned embodiment is characterized by detecting scattered light 9 that is within a range of 10° to 70° in a scattering angle θ. This arrangement of the photosensors 36 is based on the fact that light that scatters from small particles tends to be stronger in the forward direction than in the backward direction (see U.S. Pat. No. 4,739,177). Accordingly, detection efficiency can be improved.

While the photosensors 36 are located at a position in the laser beam travel direction, the photosensors 36 may also be located at a position in a direction opposite to the laser beam travel direction so that the light scattered in the backward direction indicated by the broken line 9' can be detected.

As is apparent from the foregoing, the present invention is characterized by detecting the number and size of particles entering the small detection chamber attached to the process chamber of, e.g., a semiconductor manufacturing system, using the particle detector disposed on the external atmosphere side outside the detection chamber. Therefore, the number and size of particles such as dust can be measured stably irrespective of the types of gases used and the process temperature set within the process chamber. In addition, maintenance of the particle detection system and installation thereof in a semiconductor manufacturing system can be easily executed. Further, detection sensitivity can be improved by locating photosensors at a position where the light scattered in the forward direction is effectively collected. Still further, the use of the laser beam exit window also as the scattered light exit window simplifies the design of the particle detection system.

What is claimed is:

1. A particle detection system for detecting the number and size of microscopic particles generated in a process vacuum chamber in which a semiconductor manufacturing process is performed, the process vacuum chamber being formed by an enclosure, the particle detection system comprising:

a detection chamber defining an internal space and being mounted outside the enclosure forming the process vacuum chamber so as to communicate with the process vacuum chamber, and a laser beam transmitting window means and a scattered light extracting window; and a particle detector means arranged in an external atmospheric environment outside the detection chamber and including a light-emission means for emitting a laser beam into the detection chamber through the laser beam transmitting window means and a light-detection means for detecting scattered light generated within the detection chamber through the scattered light extracting window.

2. A particle detection system as claimed in claim 1, wherein the detection chamber has a structure which is attachable to and detachable from the process vacuum chamber.

3. A particle detection system as claimed in claim 2, wherein the particle detector means is formed as a single independent unit attachable to the detection chamber from outside the detection chamber, and has a structure which is attachable to and detachable from the detection chamber.

4. A particle detection system as claimed in claim 3, wherein the particle detector means is attachable to and detachable from the detection chamber by means of an opening formed in an enclosure of the particle detector means, the detection chamber being fitted into the opening.

5. A particle detection system as claimed in claim 1, wherein the particle detector means is formed as a single independent unit attachable to the detection chamber from outside the detection chamber, and has a structure which is attachable to and detachable from the detection chamber.

6. A particle detection system as claimed in claim 5, wherein the particle detector means is attachable to and detachable from the detection chamber by means of an opening formed in an enclosure of the particle detector means, the detection chamber being fitted into the opening.

7. A particle detection system as claimed in claim 1, wherein the light-detection means is arranged at a position where it can detect scattered light generated at an angle close to 90° with respect to a laser beam path.

8. A particle detection system as claimed in claim 1, wherein the light-detection means is arranged at a position where it can detect scattered light generated at an angle within a range of 10 to 70 degrees with respect to the laser beam path.

9. A particle detection system as claimed in claim 8, wherein the laser beam transmitting window means includes the laser beam entrance window and a laser beam exit window, the laser beam exit window also being used as the scattered light extracting window.

* * * * *